(12) United States Patent
Tsiperman et al.

(10) Patent No.: US 8,207,361 B2
(45) Date of Patent: Jun. 26, 2012

(54) TIGECYCLINE CRYSTALLINE FORMS AND PROCESSES FOR PREPARATION THEREOF

(75) Inventors: Evgeny Tsiperman, Beer-Sheva (IL); Sigalit Levi, Modi'in (IL); Judith Aronhime, Rehovot (IL); Tamas Koltai, Netanya (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 13/006,719

(22) Filed: Jan. 14, 2011

(65) Prior Publication Data

US 2011/0112316 A1 May 12, 2011

Related U.S. Application Data

(62) Division of application No. 11/789,432, filed on Apr. 24, 2007, now Pat. No. 7,871,993.

(60) Provisional application No. 60/794,763, filed on Apr. 24, 2006, provisional application No. 60/796,800, filed on May 1, 2006.

(51) Int. Cl.
| C07C 43/00 | (2006.01) |
| C07C 49/00 | (2006.01) |
| C07C 237/26 | (2006.01) |
| A61K 31/65 | (2006.01) |
| A61K 31/167 | (2006.01) |
| A61P 31/04 | (2006.01) |

(52) U.S. Cl. ......... 552/205; 514/152; 514/616; 564/157
(58) Field of Classification Search .................. 552/205; 514/152, 616; 564/157
See application file for complete search history.

(56) References Cited

U.S. PATENT DOCUMENTS

| 2,980,584 A | 4/1961 | Hammer et al. |
| 2,990,331 A | 6/1961 | Neumann et al. |
| 2,997,471 A | 8/1961 | Gottstein et al. |
| 3,062,717 A | 11/1962 | Hammer et al. |
| 3,165,531 A | 1/1965 | Blackwood et al. |
| 3,454,697 A | 7/1969 | Joyner et al. |
| 3,557,280 A | 1/1971 | Weber et al. |
| 3,674,859 A | 7/1972 | Beutel et al. |
| 3,957,980 A | 5/1976 | Noseworthy |
| 4,018,889 A | 4/1977 | Armstrong |
| 4,024,272 A | 5/1977 | Rogalski et al. |
| 4,126,680 A | 11/1978 | Armstrong |
| 5,240,879 A | 8/1993 | De Bruin |
| 5,248,797 A | 9/1993 | Sum |
| 5,281,628 A | 1/1994 | Hlavka et al. |
| 5,284,963 A | 2/1994 | Sum et al. |
| 5,401,863 A | 3/1995 | Hlavka et al. |
| 5,494,903 A | 2/1996 | Hlavka et al. |
| 5,495,031 A | 2/1996 | Sum et al. |
| 5,675,030 A | 10/1997 | Krishnan et al. |
| 2006/0183720 A1 | 8/2006 | Sum et al. |
| 2006/0247181 A1 | 11/2006 | Fawzi et al. |
| 2007/0026080 A1 | 2/2007 | Chanana et al. |
| 2007/0049560 A1 | 3/2007 | Krishnan et al. |
| 2007/0049561 A1 | 3/2007 | Krishnan et al. |
| 2007/0049562 A1 | 3/2007 | Krishnan et al. |
| 2007/0049563 A1 | 3/2007 | Krishnan et al. |
| 2007/0123497 A1 | 5/2007 | Krishnan et al. |

FOREIGN PATENT DOCUMENTS

| EP | 0 535 346 | 4/1993 |
| GB | 876500 | 9/1961 |
| JP | 01-029346 | 1/1989 |
| WO | WO 2002/072031 | 9/2002 |
| WO | WO 2006/128150 | 11/2006 |
| WO | WO 2006/130431 | 12/2006 |
| WO | WO 2006/130501 | 12/2006 |
| WO | WO 2008/066935 | 6/2008 |
| WO | WO 2008/155405 | 12/2008 |

OTHER PUBLICATIONS

European Search Report for EP Application No. 11180957.0, dated Feb. 7, 2012, 4 pages.
Threlfall, Terence L., "Analysis of Organic Polymorphs: A Review", Analyst, Oct. 1995, vol. 120, pp. 2435-2460.
Bryn, Stephen, et al., "Pharmaceutical Solids: A Strategic Approach to Regulatory Considerations", Pharmaceutical Research, 1995, vol. 12, No. 7, pp. 945-954.
Measuring colour, 3rd Ed. / R.W.G. Hunt (1998).
Polymorphism in Pharmaceutical Solids, Drugs and the Pharmaceutical Sciences, vol. 95, (1999).
Anonymous, "Tygacil Scientific Discussion", EMEA 2006 http://www.infectiologie.com/site/medias/enseignment/du-lyon/Tygacil%20EPAR.pdf.
Database WPI Week 198910. Derwent Publications Ltd., London, GB: An 1989-074689, JP01029346A (Nippon Kayaku KK) Jan. 31, 1989 (Abstract).
J. Am. Chem. Soc., 75: 4621. (1953).
J.Am.Chem.Soc., 82: 1253-1254. (1960).
J.Med.Chem., 5(3): 538 (1962).
J.Med.Chem 37: 184 (1994).
Nelson et al., "Versatile and Facile Synthesis of Diverse Semisynthetic Tetracycline Derivatives via Pd-Catalyzed Reactions", Journal of Organic Chemistry, 68: 5838-5851 (2003).
Sum et al., "Synthesis and Structure—Activity Relationship of Novel Glycylcycline Derivatives Leading to the Discovery of GAR-936," *Bioorganic & Medicinal Chemistry Letters*, 9: 1459-1462 (1999).
March's Advanced Organic Chemistry: Reactions, Mechanisms, and Structure; 5th Ed., (2001).

*Primary Examiner* — Barbara P Badio
*Assistant Examiner* — Sara E Townsley
(74) *Attorney, Agent, or Firm* — Kenyon & Kenyon LLP

(57) ABSTRACT

The present invention relates to solid crystalline Tigecycline, and crystalline forms thereof.

15 Claims, 3 Drawing Sheets

TIGECYCLINE CRYSTALLINE FORMS AND PROCESSES FOR PREPARATION THEREOF

CROSS-REFERENCE TO RELATED APPLICATIONS

This present application is a divisional application of U.S. application Ser. No. 11/789,432 filed Apr. 24, 2007 now U.S. Pat. No. 7,871,993, which claims the benefit of the filing date of U.S. Provisional Patent Application No. 60/794,763 filed Apr. 24, 2006, and U.S. Provisional Patent Application No. 60/796,800 filed May 1, 2006, the disclosures of all of which are incorporated herein by reference.

FIELD OF THE INVENTION

The present invention relates to crystalline forms of Tigecycline and processes for preparing thereof.

BACKGROUND OF THE INVENTION

Tigecycline (CAS 220620-09-7), (4S,4aS,5aR,12aS)-9-(2-(tert-butylamino) acetamido)-4,7-bis(dimethylamino)-1,4,4a,5,5a,6,11,12a-octahydro-3,10,12,12a-tetrahydroxy-1,11-dioxo-2-naphthacenecarboxamide, is the first drug of a new generation of tetracycline antibiotics called glycylcyclines. Tigecycline has a wider range of bioactivity than the parent tetracycline and its analogues discovered so far. Moreover it may be administrated less frequently and/or in lower doses.

Tigecycline has been introduced and marketed by Wyeth under the brand name TYGACIL® and it is especially indicated against acute lethal infections caused by Gram-negative bacteria. TYGACIL® is marketed as lyophilized powder or cake for intravenous injection. The drug substance does not contain excipients or preservatives.

Tigecycline has the following structure:

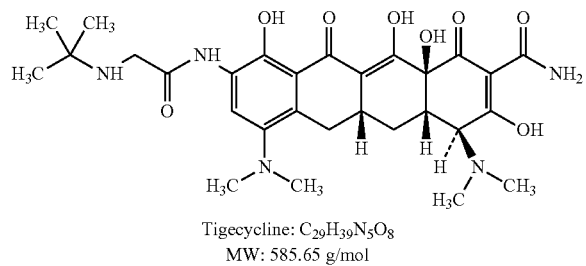

Tigecycline: $C_{29}H_{39}N_5O_8$
MW: 585.65 g/mol and was disclosed in U.S. Pat. Nos. 5,494,903 and 5,284,963.

U.S. Pat. No. 5,675,030 describes a specific method for obtaining solid Tigecycline by evaporation from a dichloromethane solution. P.C.T. Application No. WO 2006128150 discloses crystalline forms and processes thereof.

The present invention relates to the solid state physical properties of Tigecycline. These properties can be influenced by controlling the conditions under which Tigecycline is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must necessitate the use of glidants such as colloidal silicon dioxide, talc, starch, or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulation syrups, elixirs, and other liquid medicaments. The solid state form of a compound can also affect its behavior on compaction and its storage stability.

These practical physical characteristics are influenced by the conformation and orientation of molecules in the unit cell, which define a particular polymorphic form of a substance. The polymorphic form can give rise to a thermal behavior different from that of the amorphous material or another polymorphic form. Thermal behavior is measured in the laboratory by such techniques as capillary melting point, thermogravimetric analysis ("TGA"), and differential scanning calorimetry ("DSC") and can be used to distinguish some polymorphic forms from others. A particular polymorphic form can also give rise to distinct spectroscopic properties that can be detectable by powder x-ray crystallography, solid state $^{13}C$ NMR spectrometry, and infrared spectrometry.

Generally, the crystalline solid has improved chemical and physical stability over the amorphous form, and forms with low crystallinity. They can also exhibit improved hygroscopicity, bulk properties, and/or flowability.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. There is a need in the art for crystalline Tigecycline and polymorphic forms thereof.

SUMMARY OF THE INVENTION

In a first embodiment of the present invention, provided is a Tigecycline solvate. Preferably, the solvate is a methyl ethyl ketone ("MEK") solvate or an ethyl acetate solvate.

In another embodiment of the present invention, provided is a crystalline form of Tigecycline characterized by x-ray powder diffraction reflections at about 4.2, 9.1, 11.4, 14.0 and 15.7±0.2 degrees two-theta. This crystalline form may be a solvate of ethyl acetate or a solvate of MEK.

In another embodiment, the present invention provides a crystalline form of Tigecycline, characterized by x-ray powder diffraction reflections at about 9.5, 9.8, 18.1, 20.2 and 21.6±0.2 degrees two-theta.

In another aspect, the present invention provides methods for preparing the above crystalline forms.

In another aspect, the present invention provides a pharmaceutical composition comprising at least one of the crystalline Tigecycline forms described above, made by the processes of the present invention, and one or more pharmaceutically acceptable excipients.

The present invention further provides a process for preparing a pharmaceutical formulation comprising combining one or more of the crystalline Tigecycline form described above with at least one pharmaceutically acceptable excipient.

The present invention further provides for the use of at least one of the crystalline Tigecycline forms described above for the manufacture of a pharmaceutical composition for the treatment of infections.

DETAILED DESCRIPTION OF THE INVENTION

As used herein, the term "ambient temperature" refers to a temperature of between about 15° C. to about 30° C. Further, the term "spontaneous evaporation" refers to the evaporation of a solvent from a mixture, solution, or suspension without manipulating the temperature and/or pressure of the environment of such mixture, solution or suspension. In general, such spontaneous evaporation takes place at about ambient temperature and at about atmospheric pressure.

As used herein, "solvate" refers to any crystalline form which incorporates solvent at a level of more than about 1% by weight.

Figure 1:
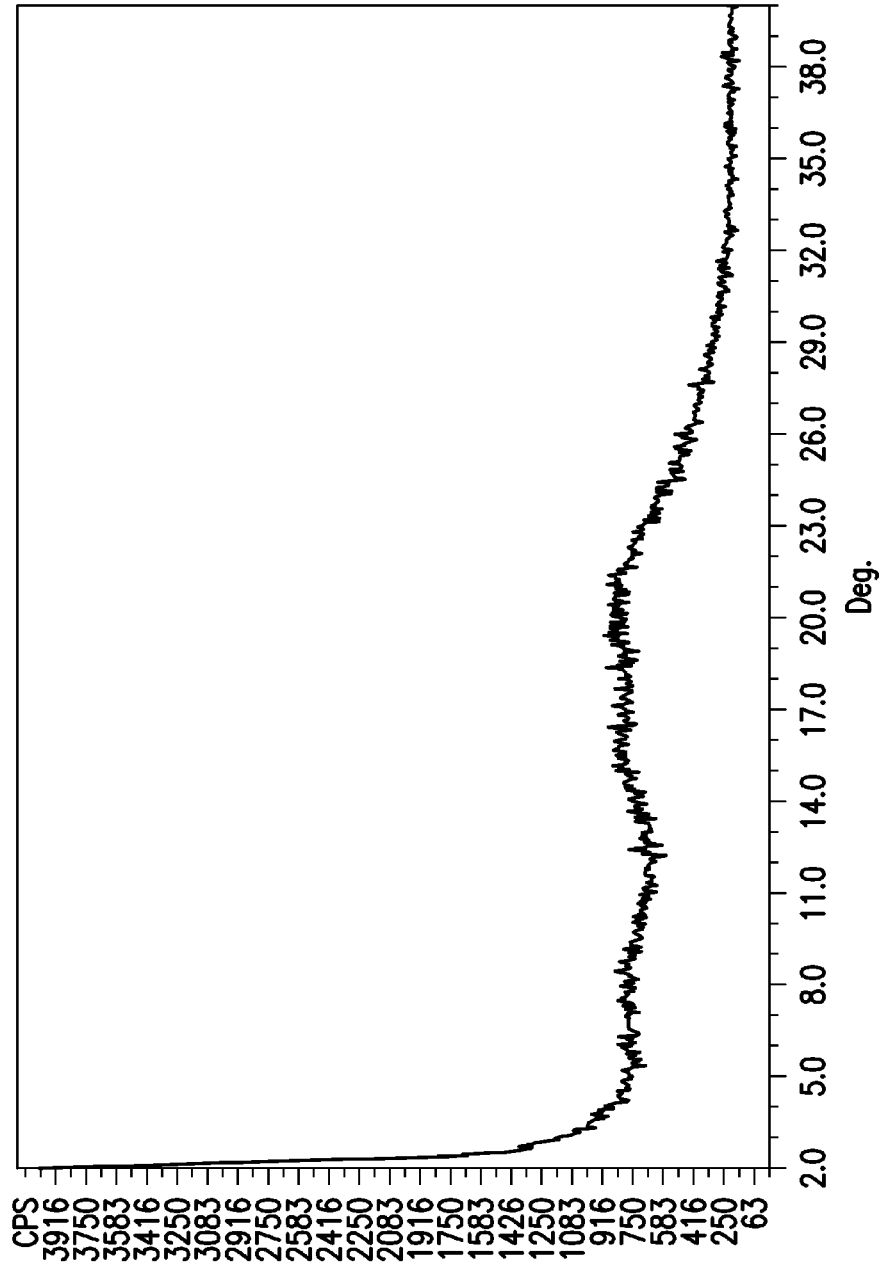
FIG. 1 illustrates a powder X-ray diffraction pattern for amorphous Tigecycline.

U.S. Pat. No. 5,675,030 mentions isolation of solid Tigecycline by evaporation from a dichloromethane solution. According to FIG. 1, repetition of the evaporation from dichloromethane step results in amorphous Tigecycline.

The present invention provides Tigecycline solvate. Preferably, the solvate is a MEK solvate or an ethyl acetate solvate.

Figure 2:
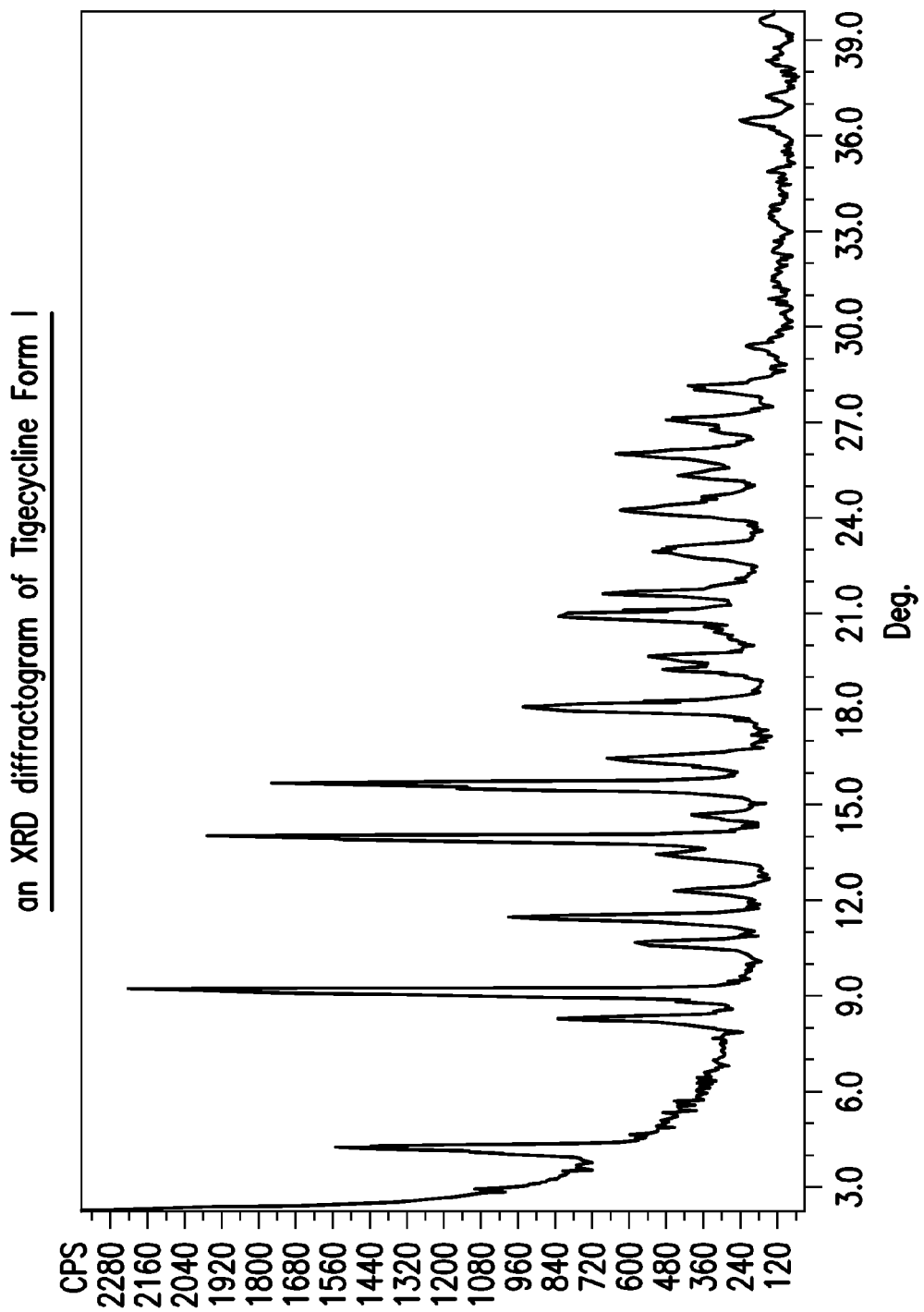
FIG. 2 illustrates a powder X-ray diffraction pattern for a Tigecycline crystalline form characterized by x-ray powder diffraction reflections at about 4.2, 9.1, 11.4, 14.0 and 15.7±0.2 degrees two-theta (as prepared by example 1).

The present invention provides a crystalline form of Tigecycline, characterized by powder x-ray diffraction reflections at about 4.2, 9.1, 11.4, 14.0 and 15.7±0.2 degrees two-theta. This crystalline form can be further characterized by powder x-ray diffraction reflections at about 8.3, 16.6, 18.1, 21.0 and 21.7±0.2 degrees two-theta, or as substantially as depicted in FIG. 2. Preferably, this crystalline form of Tigecycline is in a substantially pure form, having less than about 20% of any other Tigecycline form present, more preferably having less than about 10% of any other Tigecycline form present, even more preferably having less than about 5% of any other Tigecycline form present, and most preferably having less than about 2% of any other Tigecycline form present. This crystalline form may be a solvate of either MEK or ethyl acetate, depending on the solvent from which it is prepared.

When this form is prepared from MEK, it shows a weight loss of about 11.7% as measured by thermal gravimetric analysis ("TGA") at the range of about 25° C. to about 180° C. A water content of about 1.4% was measured by Karl Fisher for this solvate. This form is preferably a mono-solvate of MEK, and thus contains about 10% to about 12% solvent.

When this form is prepared from ethyl acetate, it showed a weight loss of about 16.5% as measured by TGA at the range of about 25° C. to about 180° C. A water content of about 0.7% was measured by Karl Fisher for this solvate.

The present invention provides processes for the preparation of the Tigecycline form described above comprising preparing and maintaining a mixture of Tigecycline, preferably amorphous Tigecycline, in a solvent selected from a saturated or aromatic $C_5$-$C_8$ hydrocarbon, a low boiling point ketone, and a low boiling point ester. Preferably the mixture is maintained for at least about an hour. Most preferably, the solvent evaporates spontaneously.

A low boiling point ketone or ester is preferably a ketone or ester having a boiling point of less than about 120° C.

Preferably, the solvent is selected from benzene, toluene, xylene, MEK, or ethyl acetate. Most preferably, the solvent is toluene.

Preferably, the mixture or solution is maintained at a temperature of between about 0° C. to about 40° C., more preferably at ambient temperature or lower. Even more preferably, the mixture is stirred.

Typically, the mixture is maintained for at least about 0.5 hours, preferably for more than about 6 hours, more preferably for between about 12 hours to about 16 hours, although the time period will vary depending on the quantity of material being crystallized, amongst other factors. Periodic powder x-ray diffraction patterns may be recorded until the desired form is obtained.

Preferably, the solvent is in a volume to weight of Tigecycline ratio of about 10 to about 30, preferably in a volume to weight ratio of about 20. Preferably, when using MEK as a solvent, the obtained precipitate is dried, even more preferably, the precipitate is dried for about 16 hours at about 40° C.

Figure 3:
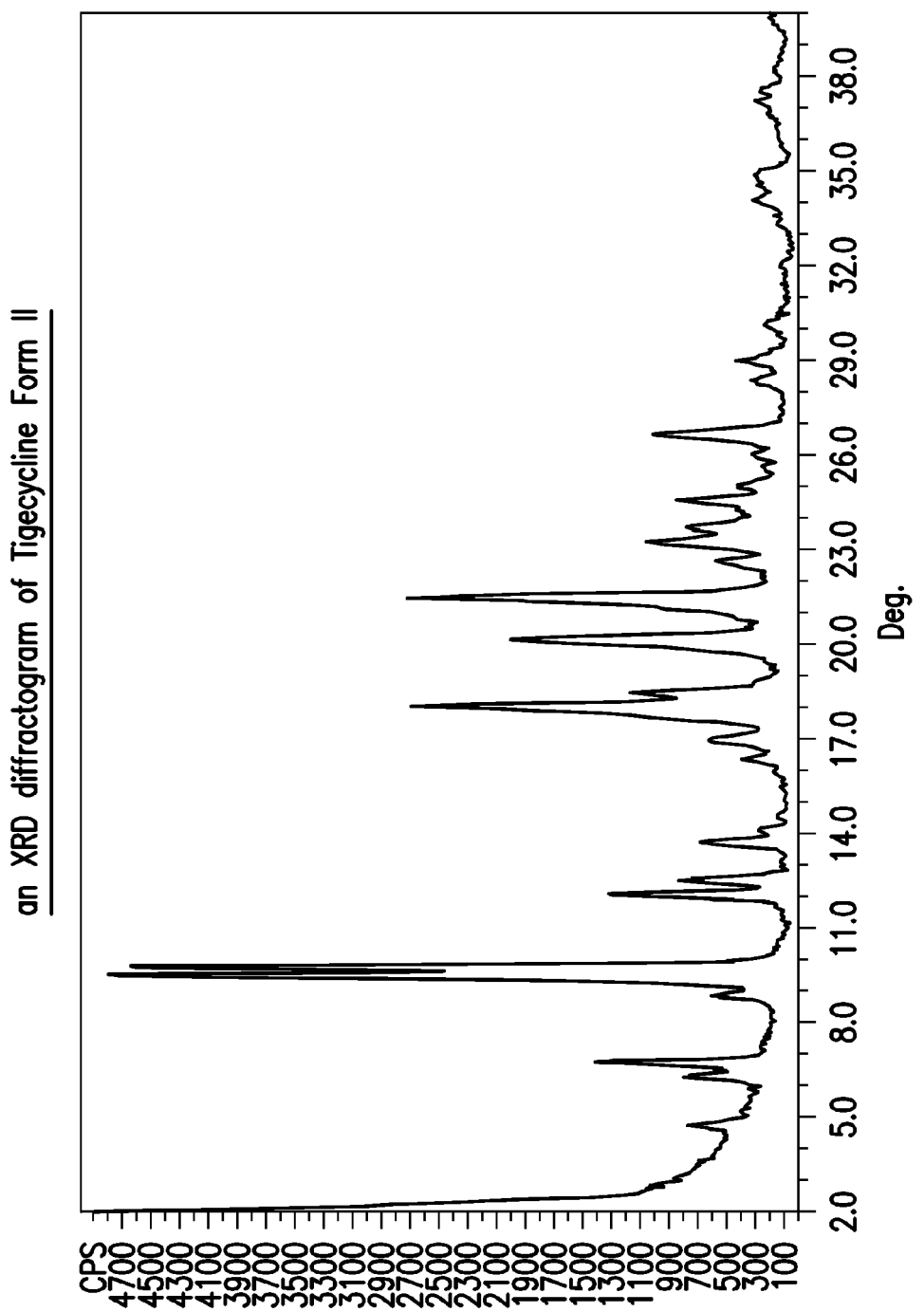
FIG. 3 illustrates a powder X-ray diffraction pattern for a Tigecycline crystalline form characterized by x-ray powder diffraction reflections at about 9.5, 9.8, 18.1, 20.2 and 21.6±0.2 degrees two-theta (as prepared by example 2).

The present invention provides another crystalline form of Tigecycline, characterized by x-ray powder diffraction reflections at about 9.5, 9.8, 18.1, 20.2 and 21.6±0.2 degrees two-theta. This crystalline form may be further characterized by x-ray powder diffraction reflections at about 6.8, 12.1, 12.6, 23.3 and 26.8±0.2 degrees two-theta, or substantially as depicted in FIG. 3. Preferably, this crystalline form of Tigecycline is substantially in pure form, having less than about 20% of any other Tigecycline forms, more preferably having less than about 10% of any other Tigecycline forms, even more preferably having less than about 5% of any other Tigecycline forms, and most preferably having less than about 2% of any other Tigecycline forms.

A weight loss of up to about 1.1% was measured by TGA at the range of about 25° C. to about 180° C. Water content of up to about 1% was measured by Karl Fisher.

The present invention provides processes for the preparation of the crystalline form of Tigecycline, characterized by x-ray powder diffraction reflections at about 9.5, 9.8, 18.1, 20.2 and 21.6±0.2 degrees two-theta, comprising preparing and maintaining a mixture of Tigecycline, preferably amorphous Tigecycline, in a solvent selected from a $C_{1-5}$ nitrile, for a period to allow solvent evaporation and precipitate formation. Preferably, the evaporation is performed at a rate in which a crystalline form is obtained. More preferably, the solvent evaporates spontaneously. Alternatively, the suspension may be filtered.

Preferably, the solvent is acetonitrile. More preferably, the solvent is in a volume to weight of Tigecycline ratio of about 10 to about 30, even more preferably the solvent is in a volume to weight ratio of about 20.

Preferably, the mixture is maintained at a temperature of about −10° C. to about 30° C., more preferably from about 0° C. to about 25° C. Even more preferably, the mixture is maintained for at least about 1 hour, although it is worthy to note that depending on certain variables, including the quantity of material being crystallized, this time will vary.

Periodic powder x-ray diffraction patterns may be taken in order to determine the time period necessary. Preferably, the mixture is stirred. Optionally, the precipitate may be dried, for example, overnight at about 30° C. to about 50° C., preferably at about 40° C.

In another aspect, this Tigecycline form may be prepared by providing a solution of Tigecycline, preferably in amorphous form, in dimethoxyethane ("DME"), and admixing an amount of n-heptane to obtain a suspension. Typically, a suspension is obtained after at least about one hour, although it is worthy to note that depending on certain variables, including the quantity of material being crystallized, this time will vary. Periodic powder x-ray diffraction patterns may be taken in order to determine the time period necessary. Preferably, the suspension may then be stirred. Preferably, the precipitated form is recovered from the suspension and dried under vacuum.

The Tigecycline crystalline forms of the present invention have a maximum particle size of about 300 µm. Preferably, these Tigecycline forms have a particle size of less than about 200 µm, more preferably having a particle size of less than about 100 µm, and most preferably having a particle size of less than about 50 µm.

The present invention further provides a process for preparing amorphous Tigecycline by exposing a crystalline form of Tigecycline characterized by powder x-ray diffraction reflections at about 4.2, 9.1, 11.4, 14.0 and 15.7±0.2 degrees two-theta to 100% room humidity for 7 days at room temperature.

In another aspect of the present invention, the present invention provides a pharmaceutical formulation comprising any one or more of the crystalline Tigecycline forms of the present invention. This pharmaceutical composition may additionally comprise at least one pharmaceutically acceptable excipient.

In another aspect of the present invention, the present invention provides a pharmaceutical composition comprising any one or more of the crystalline Tigecycline forms of the present invention made by the processes of the present invention, and one or more pharmaceutically acceptable excipients.

The present invention further encompasses a process for preparing a pharmaceutical formulation comprising combining one or more of the crystalline Tigecycline forms of the present invention, with at least one pharmaceutically acceptable excipient.

The present invention further provides for the use of a crystalline Tigecycline form, such as one of the crystalline forms of the present invention, for the manufacture of a pharmaceutical composition for the treatment of infections, including bacterial infections, Gram-negative bacterial infections, and lethal infections.

Pharmaceutical formulations of the present invention contain at least one of the crystalline Tigecycline forms of the present invention. In addition to the crystalline Tigecycline, the pharmaceutical formulations of the present invention can contain one or more excipients. Excipients including disintegrants, glidants, binders, diluents, lubricants, flavoring agents and colorants, are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and/or talc.

Solid pharmaceutical compositions that are compacted into a dosage form, such as a tablet, can include excipients whose functions include helping to bind the active ingredient and other excipients together after compression. Binders for solid pharmaceutical compositions include, for example, acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and/or starch.

The dissolution rate of a compacted solid pharmaceutical composition in the patient's stomach can be increased by the addition of a disintegrant to the composition. Disintegrants include, for example, alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and/or starch.

Glidants can be added to improve the flowability of a non-compacted solid composition and to improve the accuracy of dosing. Excipients that can function as glidants include, for example, colloidal silicon dioxide, magnesium trisilicate, powdered cellulose, starch, talc, and/or tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye.

Lubricants include, for example, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and/or zinc stearate.

Flavoring agents and/or flavor enhancers make the dosage form more palatable to the patient. Common flavoring agents and/or flavor enhancers for pharmaceutical products that can be included in the composition of the present invention include, for example, maltol, vanillin, ethyl vanillin, menthol, citric acid, fumaric acid, ethyl maltol, and/or tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Tigecycline and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse an active ingredient or other excipient that is not soluble in the liquid carrier uniformly throughout the composition. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and/or cetyl alcohol.

Liquid pharmaceutical compositions of the present invention can also contain a viscosity enhancing agent to improve the mouth-feel of the product and/or coat the lining of the gastrointestinal tract. Such agents include, for example, acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and/or xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present invention, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention can be a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient, Tigecycline, and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

The present invention also provides methods comprising administering a pharmaceutical formulation of Tigecycline. Tigecycline is preferably formulated for administration to a mammal, preferably a human, by injection. Tigecycline can be formulated, for example, as a viscous liquid solution or suspension, preferably a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The present invention also provides methods of treating infections in mammals, preferably humans, by administering a therapeutically effective amount of a crystalline form of Tigecycline, as disclosed herein.

Having described the invention, the invention is further illustrated by the following non-limiting examples. Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Polymorphism in Pharmaceutical Solids, Drugs and the Pharmaceutical Sciences, Volume 95 can be used for guidance. All references mentioned herein are incorporated in their entirety.

EXAMPLES

Experimental

X-Ray powder diffraction data were obtained by using methods known in the art, using a SCINTAG powder X-Ray diffractometer model X'TRA equipped with a solid-state detector. A Copper radiation of 1.5418 Å was used. A round aluminum sample holder with zero background was used. The scanning parameters included: range: 2° to 40° 2θ; scan mode: continuous scan; step size: 0.05°. The rate was 3°/min using spin. All peak positions are within ±0.2 degrees two theta.

Example 1

Preparation of a Tigecycline Crystalline Form Characterized by a Powder XRD Pattern Having Peaks at About 4.2, 9.1, 11.4, 14.0 and 15.7±0.2 Degrees 2-theta (Form I)

Amorphous Tigecycline powder was stirred with toluene at ambient temperature in an open vessel until the solvent evaporated. The remaining solid was collected and identified as Form I.

Example 2

Preparation of a Tigecycline Crystalline Form Characterized by a Powder XRD Pattern Having Peaks at About 9.5, 9.8, 18.1, 20.2, and 21.6±0.2 Degrees 2-theta (Form II)

Amorphous Tigecycline powder was stirred with acetonitrile at ambient temperature in an open vessel until the solvent evaporated. The remaining solid was collected and identified as Form II.

Example 3

Preparation of Tigecycline Forms I and II

A suspension of Tigecycline was prepared by mixing a solid Tigecycline sample and a solvent as listed in Table 1 in approximate amounts that correspond to the ratios listed in Table 1. The mixture was then stirred under the conditions specified in Table 1. Filtration of the suspension and air-drying of the cake afforded so-called wet material. In certain experiments (indicated in said table), the wet material was further dried overnight at about 40° C. under vacuum and the solid thus obtained is referred to as dry material.

TABLE 1

Results of the experiments according to Example 1

| Solvent | V (ml)/gr | Temp. | Time | Product | Form |
|---|---|---|---|---|---|
| MEK | 20 | RT | o/n | dry | I |
| EtOAc | 20 | RT | o/n | wet/dry | I |
| Toluene | 20 | RT | o/n | wet | I |
| acetonitrile | 20 | RT | 3 hr then 0-5° C. | dry | II |
| acetonitrile | 20 | 0-5° C. | 1 h | dry | II | o/n = overnight

Example 4

Preparation of Tigecycline Form II

A solid Tigecycline sample was dissolved in 1,2-dimethoxyethane, whereupon n-heptane was added into the resulting solution to induce precipitation. The suspension formed was stirred for about an hour at ambient temperature and then filtered. The solid thus obtained was dried overnight at about 40° C. under vacuum to afford Form II.

Example 5

Preparation of Amorphous Tigecycline

Form I, prepared from ethyl acetate (about 80 mg), was exposed to about 100% room humidity ("RH") for about 7 days at about room temperature. After the exposure, the crystal form was monitored by XRD.

| % RH | Crystal form |
|---|---|
| 100 | Amorphous |

What is claimed is:

1. A crystalline form of Tigecycline characterized by a powder XRD pattern having peaks at 4.2, 9.1, 11.4, 14.0 and 15.7±0.2 degrees 2-theta.

2. The crystalline Tigecycline of claim 1, further characterized by a powder XRD pattern having peaks at 8.3, 16.6, 18.1, 21.0, and 21.7±0.2 degrees 2 theta.

3. The crystalline Tigecycline of claim 2, further characterized by the powder XRD pattern as depicted in FIG. 2.

4. The crystalline tigecycline of claim 1, wherein said crystalline form is selected from the group consisting of a methyl ethyl ketone solvate or an ethyl acetate solvate.

5. The crystalline Tigecycline of claim 1, wherein said crystalline form is a methyl ethyl ketone solvate of Tigecycline.

6. The crystalline Tigecycline of claim 5, further characterized by a weight loss of about 11.7% as compared to the Tigecycline being crystallized, as determined by thermal gravimetric analysis.

7. The crystalline Tigecycline of claim 1, wherein said crystalline form is an ethyl acetate solvate of Tigecycline.

8. The crystalline Tigecycline of claim 7, further characterized by a weight loss of about 16.5% as compared to the Tigecycline being crystallized, as determined by thermal gravimetric analysis.

9. The crystalline Tigecycline of claim 1, wherein said crystalline Tigecycline is present in a composition having less than 20% of any other form of Tigecycline.

10. The crystalline Tigecycline of claim 9, wherein said crystalline Tigecycline is present in a composition having less than 10% of any other form of Tigecycline.

11. The crystalline Tigecycline of claim 10, wherein said crystalline Tigecycline is present in a composition having less than 5% of any other form of Tigecycline.

12. The crystalline Tigecycline of claim 11, wherein said crystalline Tigecycline is present in a composition having less than 2% of any other form of Tigecycline.

13. The crystalline Tigecycline of claim 1, wherein said crystalline Tigecycline is present in a pure form.

14. A pharmaceutical formulation comprising the crystalline form of Tigecycline of claim 1 and at least one pharmaceutically acceptable excipient.

15. A process for preparing a pharmaceutical formulation comprising combining the crystalline form of Tigecycline of claim 1 with at least one pharmaceutically acceptable excipient.

* * * * *